United States Patent
Roche et al.

(10) Patent No.: US 9,480,823 B2
(45) Date of Patent: Nov. 1, 2016

(54) PERFUSION DILATION CATHETER SYSTEM AND METHODS OF USE

(75) Inventors: Ellen Roche, Dublin (IE); Kevin O'Sullivan, Tralee (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 1182 days.

(21) Appl. No.: 13/040,729

(22) Filed: Mar. 4, 2011

(65) Prior Publication Data
US 2012/0226303 A1  Sep. 6, 2012

(51) Int. Cl.
*A61M 29/00* (2006.01)
*A61M 25/10* (2013.01)

(52) U.S. Cl.
CPC ....... *A61M 25/1002* (2013.01); *A61M 25/104* (2013.01); *A61M 2025/1093* (2013.01); *A61M 2025/1095* (2013.01)

(58) Field of Classification Search
CPC ......... A61M 25/1002; A61M 25/104; A61M 2025/1093; A61M 2025/1095
USPC ....................... 606/191, 192, 194; 604/96.01
See application file for complete search history.

(56) References Cited

U.S. PATENT DOCUMENTS

| | | |
|---|---|---|
| 4,327,736 A | 5/1982 | Inoue |
| 4,777,951 A | 10/1988 | Cribier |
| 4,787,388 A | 11/1988 | Hofmann |
| 4,819,751 A | 4/1989 | Shimada |
| 4,878,495 A | 11/1989 | Grayzel |
| 4,909,252 A | 3/1990 | Goldberger |
| 4,986,830 A | 1/1991 | Owens |
| 5,181,911 A | 1/1993 | Shturman |
| 5,226,888 A | 7/1993 | Arney |
| 5,352,199 A | 10/1994 | Tower |
| 5,649,978 A | 7/1997 | Samson |
| 5,735,816 A | 4/1998 | Lieber |
| 5,947,924 A | 9/1999 | Liprie |
| 6,780,175 B1* | 8/2004 | Sachdeva et al. ............ 604/531 |
| 7,244,242 B2* | 7/2007 | Freyman .................... 604/96.01 |
| 2003/0078539 A1* | 4/2003 | Peterson et al. ......... 604/103.01 |
| 2005/0090846 A1 | 4/2005 | Pedersen et al. |
| 2009/0299327 A1* | 12/2009 | Tilson et al. ................. 604/500 |

* cited by examiner

Primary Examiner — Diane Yabut
Assistant Examiner — Martin T Ton

(57) ABSTRACT

A system includes an elongate catheter having a self-expanding frame disposed at the distal end of the catheter. The frame includes a plurality of longitudinal struts defined by parallel slots. The frame may be constrained into a radially compressed configuration for delivery to a treatment site. A helical balloon is mounted about the frame. Upon release from the constraining mechanism, the frame returns to a heat-set radially expanded configuration to initiate dilation of a treatment site in a patient. Inflating the balloon around the expanded frame further expands the initial radial dilation of the site. Proximal and distal ends of the slots are unobstructed by the balloon to permit flow of a fluid through the slots and through a lumen defined by an interior surface of the balloon when the frame is in the radially expanded configuration.

13 Claims, 5 Drawing Sheets

PERFUSION DILATION CATHETER SYSTEM AND METHODS OF USE

FIELD OF THE INVENTION

This invention relates generally to dilatation catheter systems that do not obstruct the flow of body fluids therethrough during use in intraluminal procedures.

BACKGROUND

Calcific aortic stenosis is a common cause of acquired valvular heart disease with substantial morbidity and mortality. Its incidence increases exponentially in older patient populations. Fibrosis, degeneration and subsequent calcification are no longer believed to be passive or purely degenerative in nature, but in fact are predominantly active processes mediated by underlying cellular mechanisms. Over time, as fibrosis and calcification worsens, valve leaflets become increasingly rigid, restricting their ability to open. This, in turn, impedes the antegrade flow of blood through the heart resulting in several clinical syndromes including progressive heart failure. Other causes of deformed and stenotic aortic valvular lesions include rheumatic heart disease, as well as nonacquired (i.e. congenital) heart disease. Initial stages of stenotic valvular heart conditions are well tolerated by the patient, but when leaflet restriction becomes severe, invasive measures such as aortic valve replacement have commonly been required.

With the advent of catheter-based cardiovascular procedures, minimally invasive balloon valvuloplasty techniques were developed to dilate stenosed valves, such as calcific, rheumatic and congenitally stenosed leaflets. During this procedure, a catheter having a deflated balloon is percutaneously inserted into a vein or artery and advanced until the balloon is positioned within the heart valve needing treatment. The balloon is then inflated to dilate the diseased valve opening, disrupting the rigid sheets of calcium and thereby permitting enhanced leaflet mobility. Balloon dilation, depending on the disease process, may result not only in the development of numerous flexible hinge points within fibrosed and calcified leaflets, but also separation of fused commissures. After the leaflets have been dilated, the balloon is deflated and removed from the patient's cardiovascular system.

In many current instances, valvuloplasty is performed with polymeric balloon catheters that can achieve relatively high pressures at a fixed diameter. Balloons made of non-distensible plastic materials are expanded using fluid pressure up to a certain diameter after which, increases in fluid pressure within the balloon produce very little change in balloon diameter. These balloons can achieve high pressures for an effective therapy, but have several inherent limitations.

For example, typical catheter balloon shapes tend to completely obstruct the flow of blood through the heart while inflated. Without perfusion through or around the catheter, the catheter balloon inflation time is limited to a few seconds before risking complications due to profound hypotension. Further, calcified valves may be particularly stiff and difficult to dilate.

Examples of prior art valvuloplasty catheter designs, as well as other related catheter designs are disclosed in U.S. Pat. Nos. 4,327,736; 4,777,951; 4,787,388; 4,878,495; 4,819,751; 4,909,252; 4,986,830; 5,352,199; and 5,947,924 and U.S. Pat. Publication No. 2005/0090846. Helical dilatation balloons are disclosed in U.S. Pat. Nos. 5,181,911; 5,226,888; 5,649,978 and 5,735,816. Known helical dilatation balloons rely entirely on the inflatable balloon to achieve radial dilation forces and to achieve the final dilated diameter of the tissue at the treatment site. There may be clinical cases where the helical balloon alone is insufficient to obtain the desired radial expansion of the treatment site. Accordingly, there is a need for a balloon catheter to perform valvuloplasty while permitting perfusion through the device during the procedure and the ability to dilate heavily calcified leaflets of the valve.

SUMMARY OF THE INVENTION

An embodiment of a perfusion dilation catheter system includes a resilient tubular frame having a self-expanded configuration and including a plurality of longitudinal struts defined by a plurality of parallel slots. A sheath constrains the frame in a radially compressed configuration. An inflatable balloon is helically wrapped around and affixed to an outer surface of the frame struts leaving proximal and distal ends of the slots uncovered to permit fluid flow through the ends of the slots and through a lumen formed through the helical configuration of the balloon when the frame is in a self-expanded configuration.

In operation, the system is delivered to a treatment site, such as a diseased heart valve. The sheath is retracted to release the frame such that the frame can expand from the radially compressed configuration to the radially self-expanded configuration, which initiates mechanical dilation of the treatment site and provides a radially expanded platform to support the helical dilatation balloon. The balloon is inflated to further dilate the treatment site. Due to the open ends of the slots between the struts of the frame, blood or other fluids are permitted to flow through the device during the procedure.

DETAILED DESCRIPTION

Specific embodiments are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician.

Figure 1:
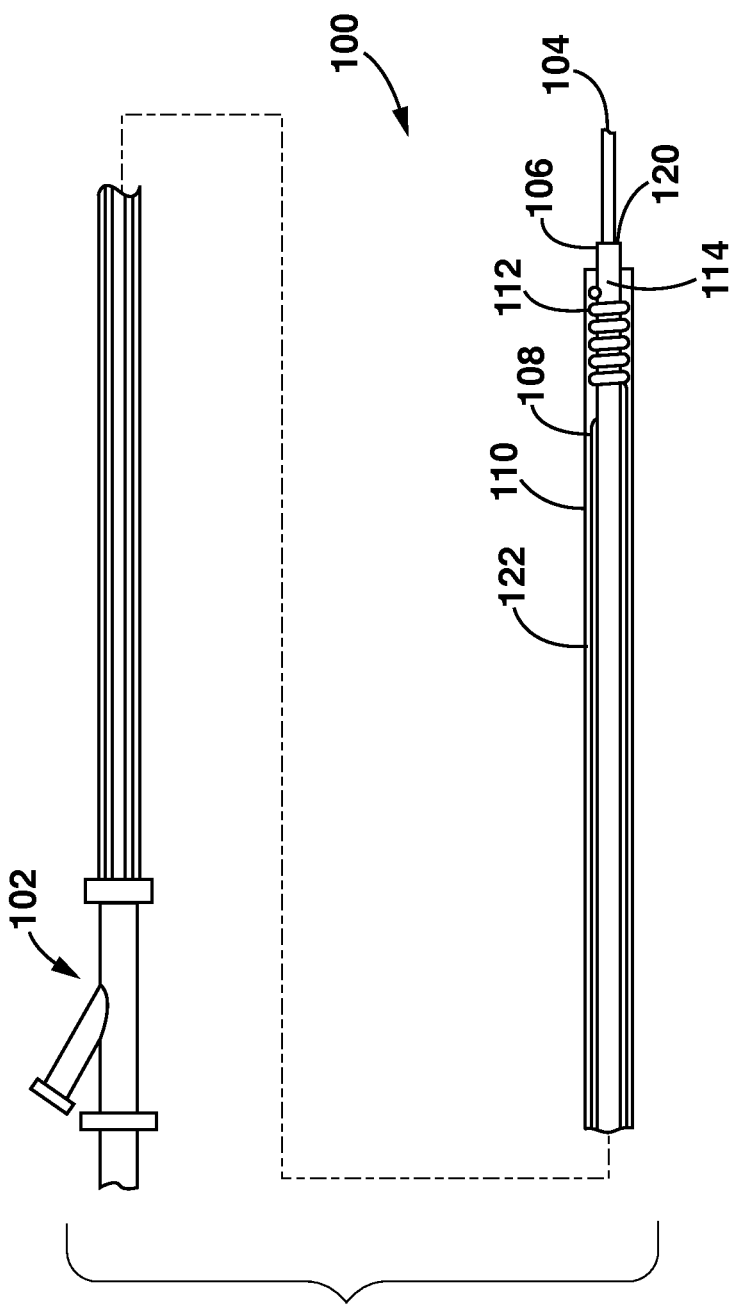
FIG. 1 is a schematic view of an embodiment of a perfusion dilatation catheter system in accordance with the disclosure.

With reference to FIG. 1, a valvuloplasty or angioplasty catheter system 100 is configured to expand at an aortic valve or at another location in a vessel. Although described herein primarily with respect to a valvuloplasty procedure at the site of an aortic valve, the apparatus and method described herein is not so limited. Instead, the apparatus and method can be used at other locations, for example and not by way of limitation, stenotic lesions in coronary arteries, veins, etc. System 100 includes at a proximal end thereof devices for access and manipulation of the different parts of system 100. For example, and not by way of limitation, a Tuohy-Borst adaptor 102 may be provided at a proximal end of system 100. Other devices, such as devices for manipulating a sleeve or sheath, may also be provided, as known to those of ordinary skill in the art.

Figure 7:
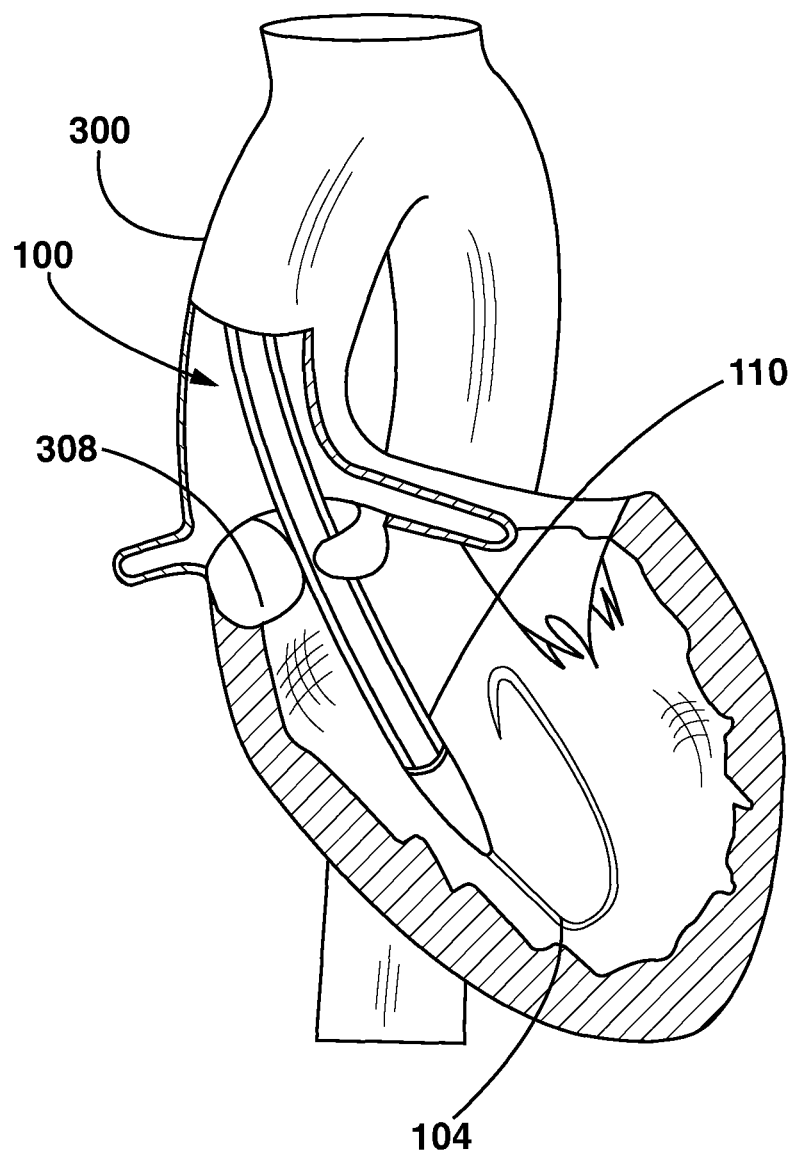
FIGS. 7-9 are schematic illustrations of progressive steps of a method of using the system of FIG. 1 in a valvuloplasty procedure.

System 100 includes an elongate tubular inner tubular shaft 106, an elongate tubular outer tubular shaft 108, and a tubular sheath or sleeve 110. Inner shaft 106 includes a lumen 120 through which a guidewire 104 may be slidably disposed. Outer shaft 108 is disposed substantially co-axially around inner shaft 106 and has an inner diameter larger than the outer diameter of inner shaft 106 such that an annular inflation lumen 122 is defined therebetween. Although outer shaft 108 is shown in this embodiment as being disposed around inner shaft 106 and system 100 is shown in an over-the-wire configuration, those of ordinary skill in the art would recognize that other catheter configurations known in the art, such as side-by-side lumen configurations or rapid exchange configurations, may also be suitable. Disposed at a distal portion of system 100 are an expandable elastic frame 114 and a helical balloon 112 mounted around the frame 114. Sheath 110 is slidably disposed around outer shaft 108, elastic frame 114 and a balloon 112 to releasably constrain frame 114 in a radially compressed configuration, as will be described in further detail below. Optionally, the distal end of inner shaft 106 may be fitted with an ogival tip that is sized and shaped to provide a smooth transition in diameter from guidewire 104 to the distal end of sheath 110, as illustrated in FIG. 7.

Inner and outer shafts 106, 108 and sheath 110 may be fabricated using materials and techniques that are well known to those of skill in the catheter arts. Suitable constructions include single or multiple layers of extruded biocompatible polymers such as polyolefin, polyamide, block copolymer, or thermo-plastic elastomer (TPE). Biocompatible metals, including without limitation, stainless steel, cobalt-chromium "super alloys" or nitinol may be incorporated as reinforcing braid filaments or as thin-walled tubing referred to as "hypotubing."

Figure 2:
FIG. 2 is a schematic illustration of a self-expanding frame of the system of FIG. 1 in its radially compressed configuration.
Figure 3:
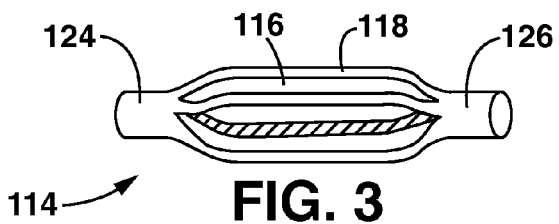
FIG. 3 is a schematic illustration of the self-expanding frame of FIG. 2 in its radially expanded configuration.
Figure 4:
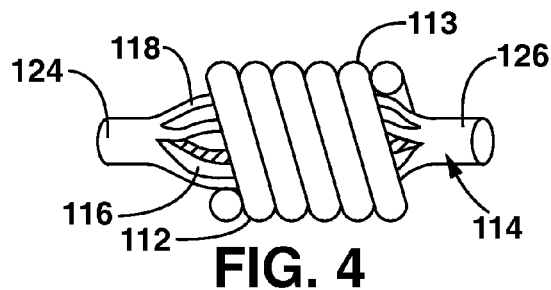
FIG. 4 is a schematic illustration of the self-expanding frame of FIG. 3 with a helical balloon mounted around it, shown in a radially expanded configuration.

FIGS. 2-6 show details of frame 114 and balloon 112. In particular, FIG. 2 shows frame 114 in its radially compressed configuration as would be achieved by constraining frame 114 within sheath 110 for delivery through the patient's vasculature. As shown in FIG. 2, frame 114 includes a plurality of longitudinal slots 116 extending through the wall of frame 114. In the embodiment shown, as can be seen in the expanded configuration illustrated in FIG. 3, there are four parallel slots 116. However, those of ordinary skill in the art would recognize that more or fewer slots may be utilized. Slots 116 define longitudinally oriented struts 118 therebetween. Frame 114 may be made from a resilient metal. Examples of resilient metals include, but are not limited to, spring temper stainless steel and "superelastic" or "pseudo-elastic" nickel-titanium alloys referred to as nitinol and being capable of forming stress induced martensite (SIM). The heat-set shape of frame 114 is its radially expanded configuration shown in FIG. 3 such that frame 114 will be in the radially expanded configuration unless an outside force deforms it into another configuration, such as the radially compressed configuration of FIG. 2. Frame 114 will return to the radially expanded configuration upon release of the outside force. Frame 114 may be integral with inner shaft 106, or may be formed separately from, then attached to inner shaft 106 such that inner shaft 106 may be made from a different material. Frame 114 includes un-slotted proximal and distal necks 124, 126 to provide secure attachment between frame 114 and inner shaft 106.

Figure 5:
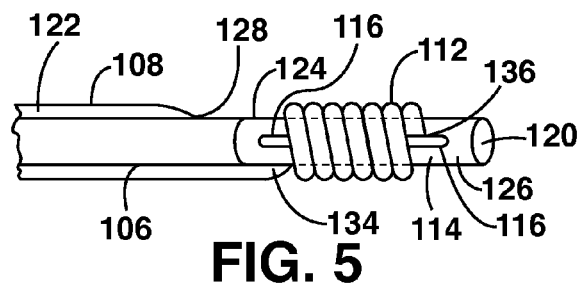
FIG. 5 is a schematic view of the self-expanding frame of FIG. 2 with a balloon helically wrapped around, shown it in a radially compressed configuration.
Figure 6:
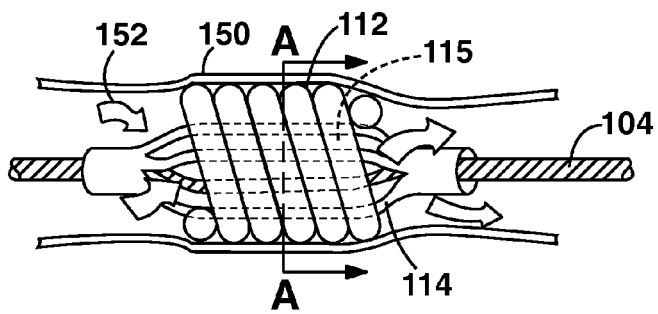
FIG. 6 is a schematic illustration of the self-expanding frame and helical balloon of FIG. 4, shown disposed in a vessel; other system components have been omitted for clarity.
Figure 6A:
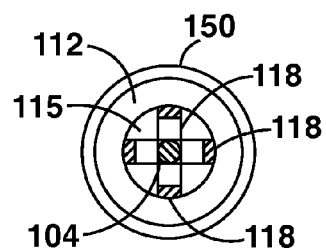
FIG. 6A is a transverse cross-sectional view of the self-expanding frame and helical balloon of FIG. 6, as viewed along the line A-A.

Helical balloon 112 is formed of inflatable tubing 113 that is attached to and extends from distal end 128 of outer shaft 108 and is spirally wrapped around frame 114, as shown in FIG. 5. At outer shaft distal end 128, a portion of outer shaft 108 is thermally fused or otherwise attached to inner shaft 106 to seal closed the distal end of inflation lumen 122 except for a fluid communication formed between inflation lumen 122 and balloon inflation lumen 134 in tubing 113. Balloon 112 may be attached to outer shaft distal end 128 by adhesive, fusion, or other means known to those of ordinary skill in the art. Balloon tubing 113 is helically wrapped around frame 114 and a distal end 136 of tubing 113 may be attached to one of struts 118 without blocking the distal ends of slots 116. Alternatively, balloon 112 may also be adhered to frame 114 where it contacts struts 118. Balloon 112 is positioned surrounding frame 114 such that proximal and distal ends of slots 116 remain uncovered by balloon 112 when frame 114 is either radially compressed or expanded. When frame 114 is permitted to resume its radially expanded configuration in the patient, the proximal and distal ends of slots 116 are thus unobstructed by balloon 112 to permit body fluid to flow through the open slot ends and through perfusion lumen 115 defined by an interior surface of helical balloon 112 as represented by arrows 152 in FIG. 6. Balloon tubing 113 may be formed of a length of extruded and stretch blow molded tubing material such as that typically used to form dilatation balloons. Non-limiting examples of suitable balloon materials include polyethylene terephthalate (PET), polyamide, polyolefin, and block copolymers.

In preparing catheter system 100 for use, balloon inflation lumen 134 is evacuated or not filled with an inflation fluid such that balloon 112 is not inflated. Un-inflated balloon 112 and frame 114 are disposed within sheath 110 such that frame 114 is forced into its radially compressed configuration. System 100 delivers frame 114 and balloon 112 to a treatment site 150 through the vasculature. At treatment site 150, the sleeve 110 is retracted to expose balloon 112 and frame 114. Frame 114 is thus permitted to return to its radially expanded configuration wherein uninflated balloon 112 is pressed against the treatment site and preliminary dilation thereof may take place in response to the radial force of the expanding frame 114. See FIG. 8.

An inflation fluid such as a dilute radiopaque contrast liquid is delivered under pressure through inflation lumen 122 to balloon lumen 134 to inflate balloon 112 by methods known to those of ordinary skill in the art. When inflated to a desired pressure, balloon 112 provides a corresponding radial dilating force and an inflated outer diameter, as disclosed by the above-mentioned U.S. patents regarding helical dilatation balloons. In the present disclosure, balloon tubing 113 also provides additional dilating forces where tubing 113 crosses over frame struts 118 when frame 114 is in the expanded configuration. In response to the selected inflation pressure, tubing 113 will tend to enlarge the annular space between expanded frame struts 118 and the tissue at treatment site 150. In this way, self-expanded frame 114 is a base or platform from which balloon tubing 113 expands to apply dilating force to the tissue and to expand the overall diameter of the frame/balloon assembly. Thus, the dilating force that may be provided by system 100 is a combination of the self-expanding force of frame 114, the dilating force of inflated balloon 112, and the inflated expansion force of tubing 113 between frame struts 118 and the treatment site. In addition, when frame 114 is in its radially expanded configuration and balloon 112 is inflated to provide a combined radial dilating force at treatment site 150, blood is permitted to flow through openings 116, as represented by arrows 152 in FIG. 6.

Figure 8:
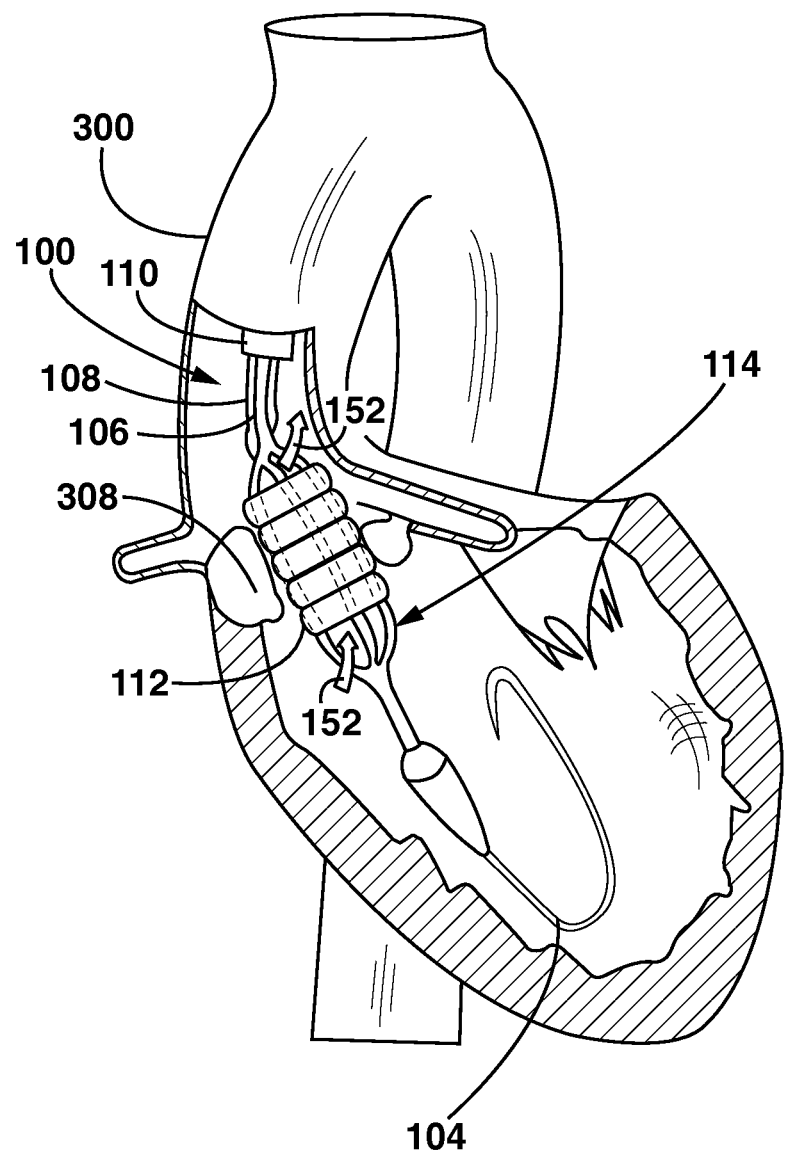
Figure 9:
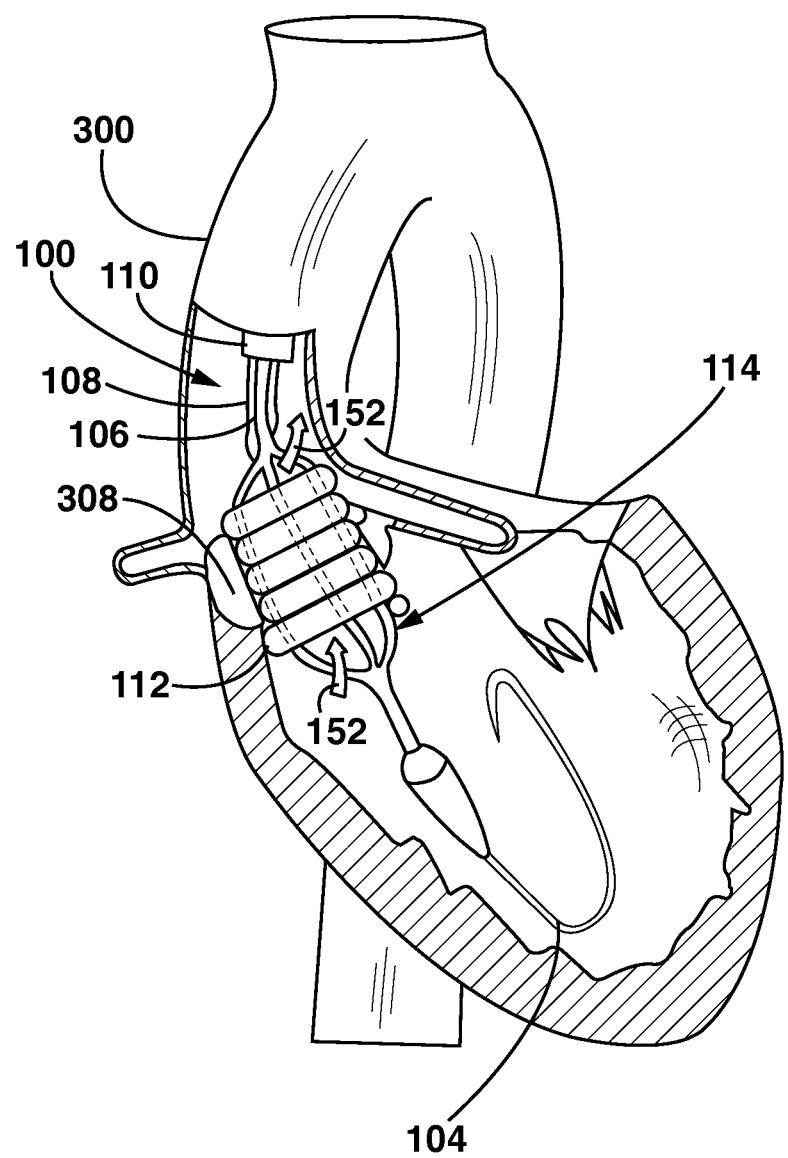

FIGS. 7-9 schematically show system 100 utilized to perform valvuloplasty, e.g., aortic valvuloplasty. Such a valvuloplasty may be utilized as an adjunct to percutaneous transcatheter heart valve replacement ("PTVR") or may be strictly a valvuloplasty procedure. As seen in FIG. 7, system 100 may be advanced in a retrograde fashion through aorta 300 over guidewire 104 and placed across a patient's stenosed aortic valve 308 using well-known percutaneous techniques. During delivery, frame 114 is constrained in the compressed delivery configuration within sheath 110 of delivery system 100 and balloon 112 is un-inflated and positioned about frame 114. Once frame 114 and balloon 112 are positioned across stenosed valve 308, sheath 110 may be retracted such that frame 114 is deconstrained and expands to its pre-set, expanded configuration, pushing uninflated balloon 112 against valve 308 to provide at least a partial or preliminary dilation of valve 308 as shown in FIG. 8. Balloon 112 shown in FIG. 8 is not yet inflated. Open proximal and distal ends of expanded slots 116 permit blood flow through a perfusion lumen 115 defined by an interior surface of deflated helical balloon 112, which is held open by expanded frame 114. Thus, blood is able to flow through valve 308 during the dilation procedure, as indicated by arrows 152.

Next, balloon 112 is inflated to further dilate valve 308, as shown in FIG. 9. The radial dilating force and balloon diameter achieved within valve 308 is a result of a combination of the mechanical expansion force of frame 114, the radial dilation force of inflated helical balloon 112 and the force generated as the balloon tubing 113 is inflated in the annular space between expanded frame struts 118 and calcified valve 308. While balloon 112 is inflated, blood continues to flow from the patient's ventricle into the aortic root through the perfusion lumen defined by the interior surface of now-inflated helical balloon 112. Balloon 112 may be inflated after sheath 110 is retracted, or simultaneously with the retraction of sheath 110. After completion of the valvuloplasty procedure, the inflation fluid is evacuated from balloon lumen 134 to deflate balloon 112, and frame 114, with the deflated balloon 112, may be positioned within sheath 110 to return frame 114 to its radially compressed configuration for removal from the patient.

The use of expandable frame 114 provides a radially enlarged platform for balloon 112 to expand from when inflated. System 100 is thus expected to provide dilation of body tissues at a greater radial force and/or to a greater diameter than is typically achieved with known cylindrical, non-perfusion dilatation balloons or known helical dilatation balloons. The size of the expanded frame 114 and balloon 112 may vary depending on the intended type of procedure. For example, and not by way of limitation, for an aortic valvuloplasty procedure in an adult human, the total expanded outer diameter including balloon 112 and frame 114 may be at least 20 mm.

While various embodiments according to the present invention have been described above, it should be understood that they have been presented by way of illustration and example only, and not limitation. Although a perfusion valvuloplasty procedure has been described herein, the devices and methods described can be used for other procedures where perfusion dilatation is considered advantageous. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. A perfusion dilatation catheter system comprising:
 a resilient tubular frame having a plurality of longitudinal struts defined by a plurality of slots, the frame being heat set in a radially expanded configuration and being adapted to be constrained in a radially compressed configuration; and
 an inflatable dilatation balloon helically wrapped around the frame struts,
 wherein each longitudinal strut extends from a first location proximal of the helically wrapped balloon to a second location distal of the helically wrapped balloon, and
 wherein adjacent windings of the helically wrapped balloon are in contact with each other when the balloon is in an inflated configuration and a lumen is defined by an interior surface of the balloon when the frame is in the radially expanded configuration.

2. The system of claim 1, wherein the frame is made from a metal alloy capable of forming stress induced martensite (SIM).

3. The system of claim 1 further comprising an elongate tubular inner shaft coupled to a proximal end of the frame, wherein the inner shaft includes a guidewire lumen extending therethrough.

4. The system of claim 3 further comprising an elongate tubular outer shaft surrounding the inner shaft to define an inflation lumen therebetween, an outer shaft distal end being coupled to a proximal end of the balloon, wherein the inflation lumen communicates with a lumen of the balloon.

5. The system of claim 1 further comprising a retractable sheath slidably disposed over the frame and balloon, wherein the sheath is configured to constrain the frame in the radially compressed configuration.

6. The system of claim 1, wherein the frame includes four struts defined by four slots.

7. A method of radially expanding a site in a vessel of a patient comprising the steps of:
 delivering a guidewire to the site;
 delivering a system over the guidewire, the system including,
  a radially self-expanding frame constrained in a radially compressed configuration, the frame having a plurality of longitudinal struts with slots disposed between the struts, and
  an inflatable helical dilating balloon fixedly mounted about the frame;

expanding the frame from the radially compressed configuration to a radially expanded configuration, wherein each of the longitudinal struts extends from a first location proximal of the balloon to a second location distal of the balloon such that the system is configured to permit fluid flow through the frame and through a perfusion lumen defined by an inner surface of the balloon when the frame is in the radially expanded configuration; and inflating the balloon.

8. The method of claim 7, wherein the frame is heat-set to the radially expanded configuration and is made from a metal capable of forming stress induced martensite, and wherein the step of expanding the frame comprises releasing the frame from a force radially compressing the frame into the radially compressed configuration.

9. The method of claim 8, wherein the step of releasing the frame from the force comprises retracting a sheath.

10. The method of claim 8, wherein the shape memory material is a nickel-titanium alloy.

11. The method of claim 7, wherein the site is an aortic valve.

12. The method of claim 7, wherein the site is a coronary artery.

13. The method of claim 7, wherein the site is an aorta.

* * * * *